United States Patent [19]

Swan

[11] Patent Number: 5,306,373
[45] Date of Patent: Apr. 26, 1994

[54] LASER RADIATION BARRIER

[76] Inventor: Charles H. Swan, 1405 S. 14th St., Dade City, Fla. 33525

[21] Appl. No.: 62,310

[22] Filed: May 14, 1993

Related U.S. Application Data

[62] Division of Ser. No. 826,011, Jan. 27, 1992, Pat. No. 5,212,387.

[51] Int. Cl.$^5$ .............. B29C 43/24; A61B 19/08; A61F 13/00
[52] U.S. Cl. .................. 156/242; 156/243; 156/245; 264/175; 250/515.1; 250/519.1; 606/2
[58] Field of Search ........... 156/242, 243, 245; 264/175; 250/515.1, 516.1, 519.1; 128/49; 606/2

[56] References Cited

U.S. PATENT DOCUMENTS

| | | | |
|---|---|---|---|
| 1,611,218 | 12/1926 | Mell | 264/175 |
| 4,114,985 | 9/1978 | Friedman | |
| 4,174,419 | 11/1979 | Nieman | 428/457 |
| 4,520,814 | 6/1985 | Weeks | |
| 4,558,093 | 12/1985 | Hatzenbuhler | 128/849 |
| 4,559,248 | 12/1985 | Sumiyoshi et al. | |
| 4,616,641 | 10/1986 | Teeple | 606/2 |
| 4,650,287 | 3/1987 | Kudo et al. | |
| 4,685,987 | 8/1987 | Fick | |
| 4,689,262 | 8/1987 | Bloom | |
| 4,715,366 | 12/1987 | Teeple | |
| 4,901,738 | 2/1990 | Brink et al. | 128/849 |
| 4,961,989 | 10/1990 | Grimwood | |
| 4,980,564 | 12/1990 | Steelmon | |
| 4,994,317 | 2/1991 | Dugan et al. | |
| 5,014,723 | 5/1991 | Kaufman | 128/853 |
| 5,059,807 | 10/1991 | Kersten et al. | 250/516.1 |
| 5,245,195 | 9/1993 | Shah et al. | 250/519.1 |

Primary Examiner—Caleb Weston
Attorney, Agent, or Firm—Frijouf, Rust & Pyle

[57] ABSTRACT

An apparatus and method is disclosed for an improved laser radiation barrier for shielding a surface from laser radiation comprising an outer polymeric layer comprising a dispersion of mica, an intermediate mica layer for retarding the penetration of the laser radiation therethrough and an inner polymeric layer comprising a dispersion of mica bounded to the intermediate mica layer. The polymeric layers comprises a dispersion of titanium dioxide. An optical metallic barrier may be interposed between the outer polymeric layer and the intermediate mica layer for distributing thermal energy.

15 Claims, 7 Drawing Sheets

LASER RADIATION BARRIER

This application is a divisional of application Ser. No. 07/826,011 filed Jan. 27, 1992, U.S. Pat. No. 5,212,387, the disclosure of which is incorporated herein by reference.

BACKGROUND OF THE INVENTION

1. Field of the Invention

This invention relates to barriers for shielding laser radiation and more particularly, to an apparatus, composition and method for an improved laser radiation barrier for shielding a surface from laser radiation.

2. Background Information

Various types of shields have been proposed in the prior art for inhibiting the penetration of radiation such as laser radiation. U.S. Pat. No. 4,980,5645 discloses a composite for blocking electromagnetic radiation including a central layer of wire reinforced glass fabric, an outer exposure coating of materials which absorb the radiation, and an inner layer of metal.

U.S. Pat. No. 4,650,287 discloses a laser-light shield including a metallic substrate having uneven surface and a flame-sprayed film formed on the uneven surface and essentially consisting of metal oxide. The shield is claimed to be useful for shielding a human body from laser light.

U.S. Pat. No. 4,689,262 discloses a composition of porcelain substrates employing alternating layers of wire cloth and porcelain green sheet material wherein the alternating layers are compressed toward one another at a somewhat elevated temperature and then kiln fired at a further elevated temperature to form a glazed porcelain surface for receiving further electrical circuitry, for example, of the microelectronic type. U.S. Pat. No. 4,961,989 discloses a coherent fire-resisting flexible sheet material for aerospace applications consisting of a layer of ceramic fibers embedded in a silicone rubber compound. The ceramic fibers may be in the form of a plain woven fabric of monofilament fibers of alumino-boro-silicate and the silicone rubber compound can be a curable non-foaming methylphenyl silicone compound. The silicone compound is applied to the fabric as a thixotropic paste in sufficient quantity to entirely cover and impregnate the fabric and is forced through the interstices of the fabric by the application of pressure. The coated and impregnated fabric is then placed in an oven to cure the silicone compound.

U.S. Pat. No. 4,901,738 discloses a laser shield constructed from a non-limiting fabric sheet and a metal layer. The shield can be used as a laser-resistant surgical drape during laser surgery to protect the patient from aberrant laser strikes. The laser shield is claimed to be resistant to penetration by commonly-used surgical lasers and is non-reflective and flame resistant.

U.S. Pat. No. 4,685,987 discloses a relatively thin broad-area dielectric interfacing composed of dual filled layers of complaint silicone rubber in sandwiching relation to a porous glass-cloth carrier, one of the layers being pre-vulcanized and the other being subsequently cured and bonded in place once the composite interfacing has been applied to heat-sink surfaces adapted to abutment with the device for the intended heat transfer.

U.S. Pat. No. 4,715,366 discloses a surgical shield for use during surgical procedures in which lasers are utilized and which comprises a fabric inner sheet interpositioned between a pair of coextensive metal foil sheets.

U.S. Pat. No. 4,994,317 discloses a fabric suitable for use as a flame barrier fabric comprising a flame durable textile fabric substrate, a flexible silicone polymer layer which stays intact, maintains its integrity on exposure to a flame and is carried by the surface of the textile fabric substrate, and a reflective flame durable paint coating carried by the silicone polymer coating.

U.S. Pat. No. 4,114,985 discloses a shield for high power infrared laser beams incorporating two spaced, juxtaposed, ceramic sheet members. The beam intercepting member has a thickness to beam power density relationship that allows opaque to translucent conversion of the portion thereof illuminated by the beam. The translucent portion subsequently diffuses the beam. The diffused beam is then absorbed by the second ceramic sheet member.

U.S. Pat. No. 4,559,248 discloses a sliding member wherein a sheet-like heat resistant material comprising expanded graphite, mica, etc. singularly or in combination, and a reinforcing material comprising either a combination of a mesh made of metal fine wires with a mesh made by weaving or knitting metal fine wires and fluoroplastic yarns together, or a mesh made by weaving knitting metal fine wires and fluoroplastic yarns together are integral shaped so that at lest on the sliding surface the metal fine wires and the fluoroplastic yarns are exposed, both constituting the reinforcing material, and the heat resistant material held by the metal fine wires and filling the meshes of the mesh as well as the voids formed between the metal fine wires in a mutually intermingled state, exhibiting a smooth surface.

U.S. Pat. No. 4,520,814 discloses an elastomeric back-up pad having a smooth laser-resistant coating thereon is provided for insertion between tissue layers incised during surgical procedures in which a laser is used to incise the tissue. The laser-resistant coating on the pad comprises a mixture of powdered metal which tends to reflect the laser beam and an elastomer which bonds the coating to the pad and imparts a smooth exterior surface to the coating thereby reducing the risk of tissue trauma as the pad is inserted between the tissue layers.

Although the aforementioned patents have contributed to the art, none of these prior art developments has provided a simple, inexpensive and reliable laser shield for common use.

Therefore, it is an object of the present invention to provide an improved laser radiation barrier for shielding a surface from laser radiation having superior resistance to laser radiation.

Another object of this invention is to provide an improved laser radiation barrier for shielding a surface from laser radiation which may be formed or molded into various shapes and contours.

Another object of this invention is to provide an improved laser radiation barrier for shielding a surface from laser radiation which is fabricated from readily available and inexpensive materials.

Another object of this invention is to provide an improved laser radiation barrier for shielding a surface from laser radiation which is fabricated from non-toxic materials for medical applications.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention with in the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved laser radiation barrier for shielding a surface from laser radiation comprising an outer polymeric layer comprising a dispersion of mica and an intermediate mica layer for retarding the penetration of the laser radiation therethrough. An inner polymeric layer comprising a dispersion of mica is bounded to the intermediate mica layer.

In a more specific embodiment of the invention, the outer polymeric layer comprises a dispersion of titanium dioxide with the titanium dioxide and the mica of the outer polymeric layer forming a ceramic creator upon impingement of the laser radiation for retarding the penetration of the laser radiation therethrough. Preferably, the inner polymeric layer comprises a dispersion of titanium dioxide.

In one embodiment of the invention, the improved laser radiation barrier includes a metallic barrier interposed between the outer polymeric layer and the intermediate mica layer for distributing thermal-energy. The metallic barrier comprises a metallic foil having a plurality of perforations.

The invention is also incorporated into the method of producing an improved laser radiation barrier for shielding a surface from laser radiation comprising the steps of mixing a first mixture comprising a silicone polymer compound and a first filler on a roll mill. The first mixture is heated to liberate volatile components. A second mixture comprising a silicone polymer compound and a second filler is mixed on a roll mill. The second mixture is heated to liberate volatile components. The first and the second mixtures are mixed with a catalyst on a roll mill to create a final catalyzed mixture. A first layer of the final catalyzed mixture is placed in a mold and a mica sheet is placed upon the first layer of the final catalyzed mixture. A second layer of the final catalyzed mixture is then placed in the mold and the final catalyzed material is cured. An optical metallic barrier may be interposed between the second layer of the final catalyzed material and the intermediate mica sheet.

In a more specific embodiment of the process, the silicone polymer compound comprises room temperature vulcanizing (RTV) silicone polymers and platinum based catalyst materials. In the alternative, the silicone polymer compound comprises silica reinforced R gum silicone polymers and peroxide based catalyst materials. The first filler comprises Titanium Dioxide (TiO$_2$) whereas the second filler comprises MICA. The final catalyzed material comprises a ceramic clay.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1:
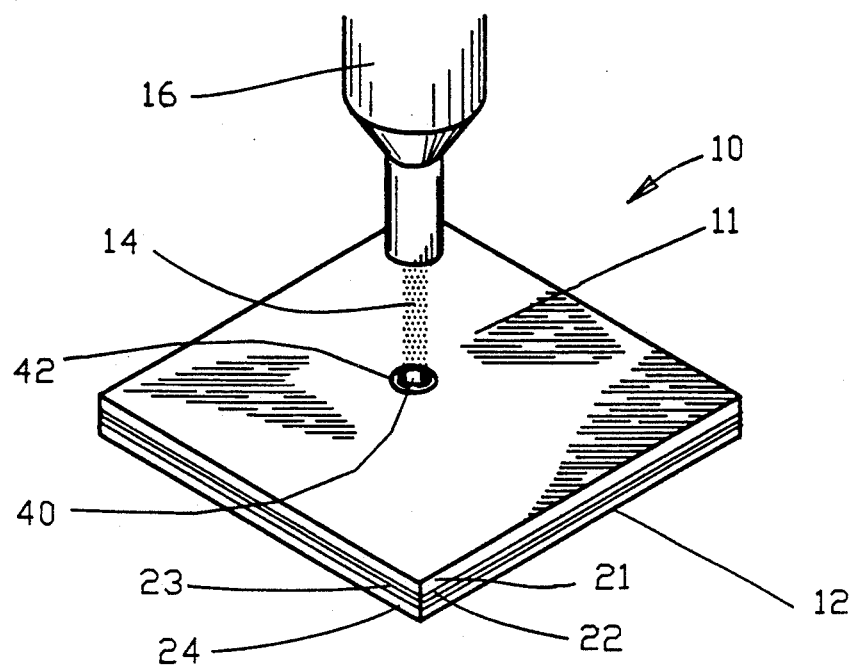
FIG. 1 is an isometric view of a first embodiment of an improved laser radiation barrier of the present invention receiving laser radiation.

FIG. 1 is an isometric view of a first embodiment of an improved laser radiation barrier 10 for shielding a top surface 11 and a bottom surface 12 from laser radiation 14 emanating from a laser device 16. Although the laser device 16 is shown as a medical laser device, it should be understood that the present invention is useful for use with virtually all types of laser including ruby, $CO_2$, yttrium aluminium garnet (YAG) and KTP lasers.

Figure 2:
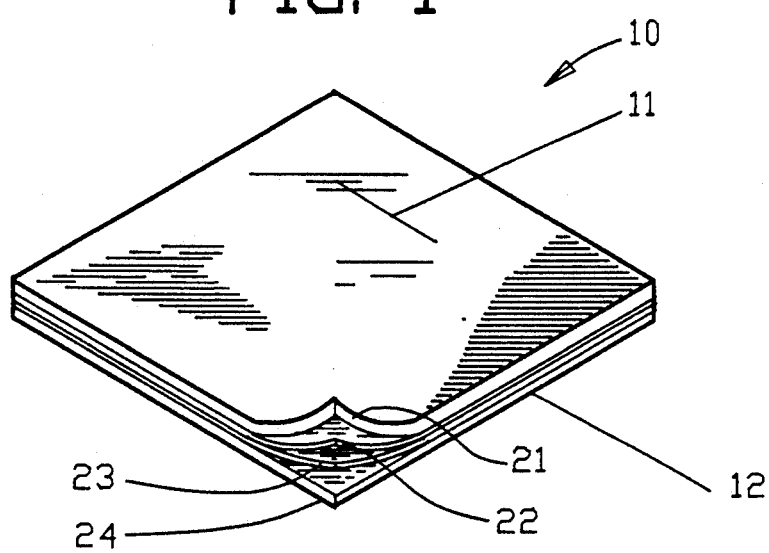
FIG. 2 is a partially pealed away isometric view of the first embodiment of the improved laser radiation barrier of FIG. 1.

FIG. 2 is a partially pealed away isometric view of the first embodiment of the improved laser radiation barrier of FIG. 1 illustrating an outer polymeric layer 21 comprising a dispersion of polymeric material such as silicone or the like, titanium dioxide and mica in particulate form. A metallic barrier layer 22 is interposed between the outer polymeric layer 21 and an intermediate mica layer 23. The intermediate mica layer 23 affixed to an inner polymeric layer 24 defining the inner surface 12.

Figure 3:
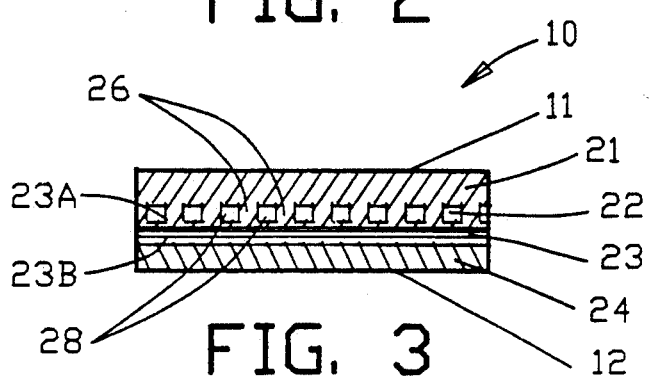
FIG. 3 is an enlarged side sectional view of the improved laser radiation barrier of FIG. 1.

FIG. 3 is an enlarged side sectional view of the improved laser radiation barrier of FIG. 1 illustrating the metallic barrier layer 22 as including a plurality of perforations 26 having a cross-sectional area greater than the cross-sectional area of supports 28. Although various types of metallic barriers have been found to be useful with the present invention, a copper foil is the preferred material for the metallic barrier layer 22. If flexibility is desired to the laser radiation barrier 10, the copper foil is preferably annealed through a conventional process.

A top surface 23A of the intermediate mica layer 23 is bonded to outer polymeric layer 21 by the outer polymeric layer 21 extending through the plurality of perforations 28 in the metallic barrier layer 22. The inner polymeric layer 24 is bonded to the inner side 23B of the mica layer.

Figure 4:
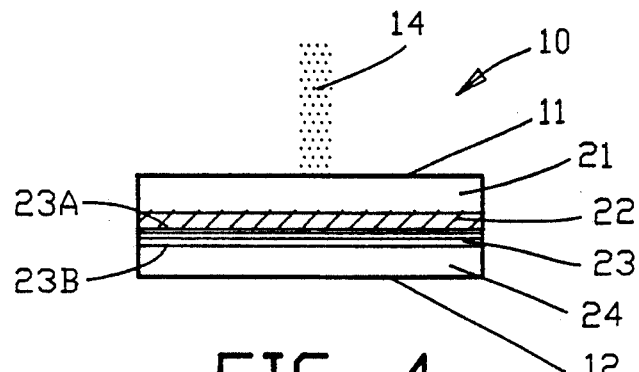
FIG. 4 is an enlarged side sectional view illustrating the first embodiment of the improved laser radiation barrier of the present invention initially receiving laser radiation.

FIG. 4 is an enlarged side view of the laser radiation barrier 10 first receiving the laser radiation 14 from the laser 16.

Figure 5:
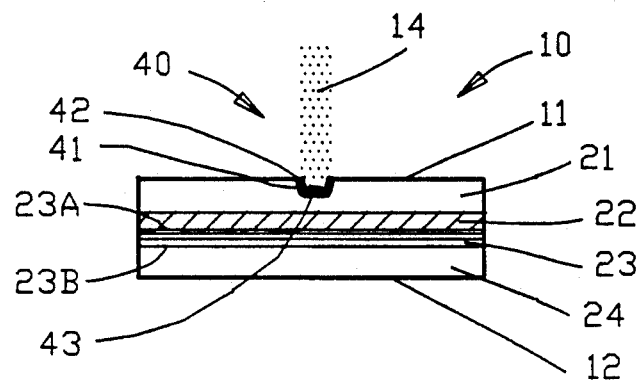
FIG. 5 is a view similar to FIG. 4 illustrating a ceramic crater being formed in an outer polymeric layer by the laser radiation.

FIG. 5 illustrates the penetration of the laser radiation 14 into the outer polymeric layer 21 to form a crater 40. The crater 40 includes a crater sidewall 41 terminating in a crater lip 42 with a moltant bead 43 at the bottom of the crater 40.

Figure 6:
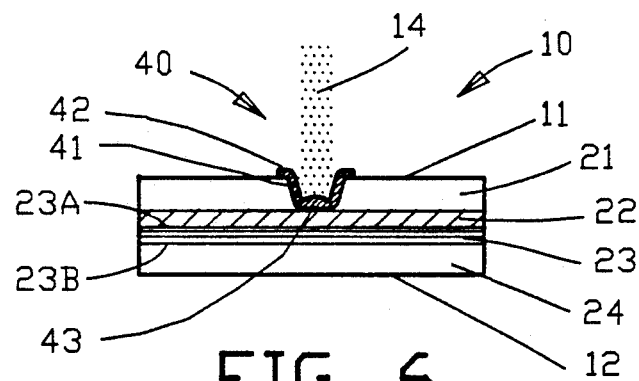
FIG. 6 is a view similar to FIG. 5 illustrating an intermediate metallic layer dissipating the heat generated by the laser radiation.

FIG. 6 illustrates the further penetration of the laser radiation 14 into the outer polymeric layer 21 with the crater sidewall 41 being enlarged and with the bead 43 being disposed adjacent the metallic barrier layer 22. The beam 43 transfers heat to the metallic barrier layer 22 whereat the metallic barrier layer 22 disperses heat away from the bead 43. The crater sidewall 41 is solidified and inhibits the heat of the bead 43 from dispersing horizontally in FIG. 6 through the outer polymeric layer. The intermediate mica layer 23 acts as an insulator to the inner polymeric layer 24.

Figure 7:
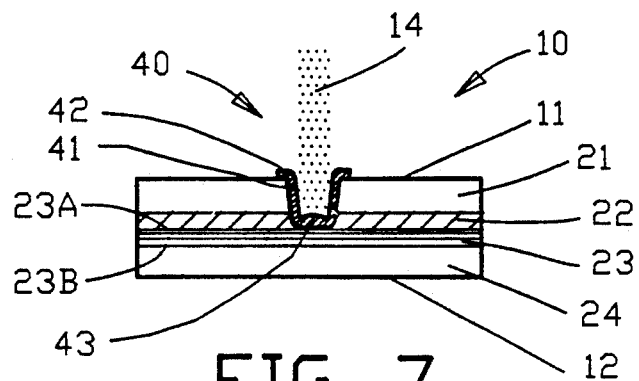
FIG. 7 is a view similar to FIG. 6 illustrating the intermediate mica layer retarding the penetration of the laser radiation therethrough.

FIG. 7 illustrates the continued penetration of the laser radiation 14 whereat the bead 43 has burned through the metallic barrier layer 22 and is impacting upon the intermediate mica layer 23. The intermediate mica layer 23 continues to thermally insulate the inner polymeric layer 24 from the laser radiation 14.

Figure 8:
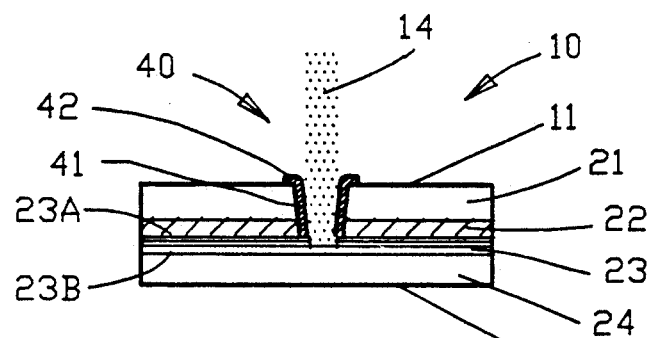
FIG. 8 is a view similar to FIG. 7 illustrating a partial penetration of the intermediate mica layer by the laser radiation.

FIG. 8 illustrates the laser radiation 14 partially burning through the mica layer 23. The mica layer 23 continues to thermally insulate the inner polymeric layer 24 from the laser radiation 14. As it can be seen from FIG. 8, the bead 43 has dissipated and the mica layer 23 receives the full radiation 14 from the laser 16.

Figure 9:
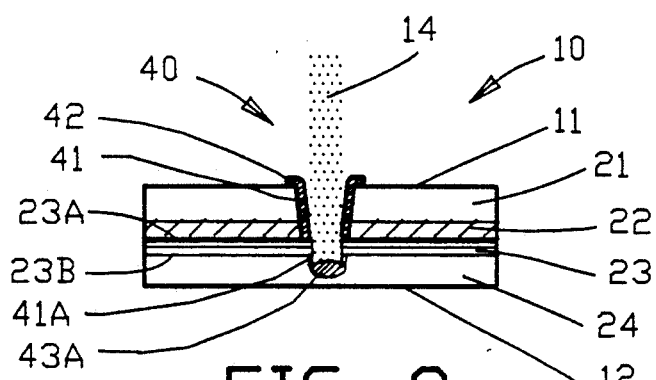
FIG. 9 is a view similar to FIG. 8 illustrating a ceramic crater being formed in an inner polymeric layer by the laser radiation.

FIG. 9 illustrates the completion of penetration of the laser radiation 14 through the mica layer 23 and the commencement of penetration through the inner polymeric layer 24. As it can be seen from FIG. 9, the crater 40 has reformed with a new bead 43A and a new crater sidewall 41A.

Figure 10:
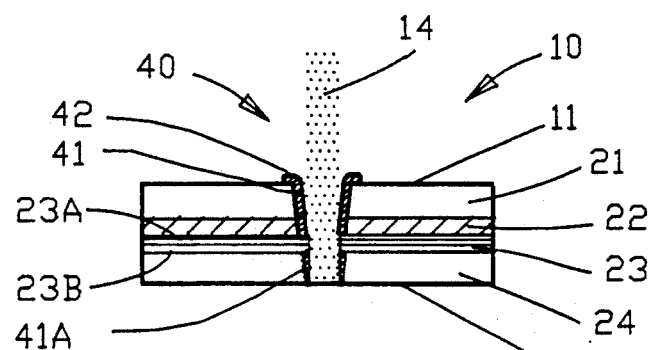
FIG. 10 is a view similar to FIG. 9 illustrating a total penetration of the laser radiation barrier by the laser radiation.

FIG. 10 illustrates the completion of burning of the laser radiation 14 through the inner polymeric layer 24.

Figure 11:
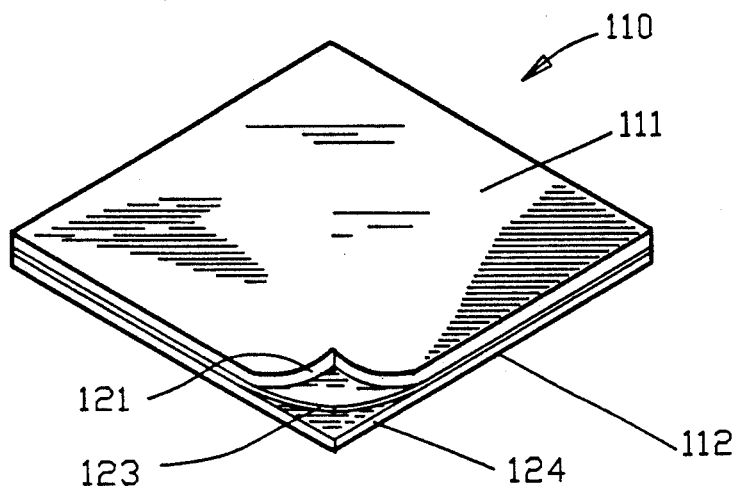
FIG. 11 is a partially pealed away isometric view of a second embodiment of the improved laser radiation barrier.

FIG. 11 is a partially pealed away isometric view of a second embodiment of an improved laser radiation barrier 110 for shielding a top surface 111 and a bottom surface 112 from laser radiation 14 emanating from the laser device 16.

The improved laser radiation barrier 110 includes an outer polymeric layer 121 comprising a dispersion of polymeric material such as silicone or the like, titanium dioxide and mica in particulate form. An intermediate mica layer 123 is interposed between the outer polymeric layer 121 and an inner polymeric layer 124 defining the inner surface 112.

Figure 12:
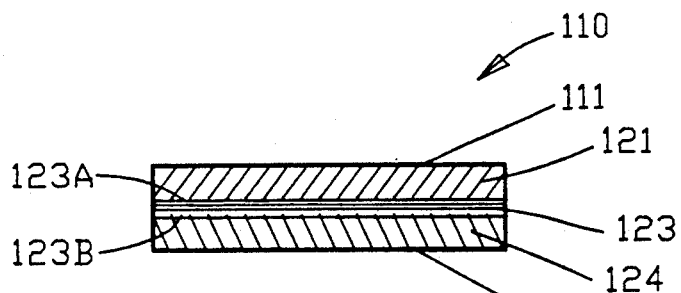
FIG. 12 is an enlarged side sectional view of the improved laser radiation barrier of FIG. 11.

FIG. 12 is an enlarged side sectional view of the improved laser radiation barrier of FIG. 11. A top surface 123A of the intermediate mica layer 123 is bonded to outer polymeric layer 121 and a bottom surface 123B of the intermediate mica layer 123 is bonded to the inner polymeric layer 124.

Figure 13:
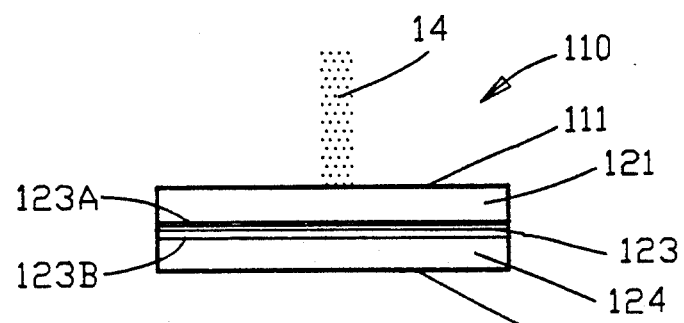
FIG. 13 is an enlarged side sectional view illustrating the second embodiment of the improved laser radiation barrier of the present invention initially receiving laser radiation.

FIG. 13 is an enlarged side view of the laser radiation barrier 110 first receiving the laser radiation 14 from the laser 16.

Figure 14:
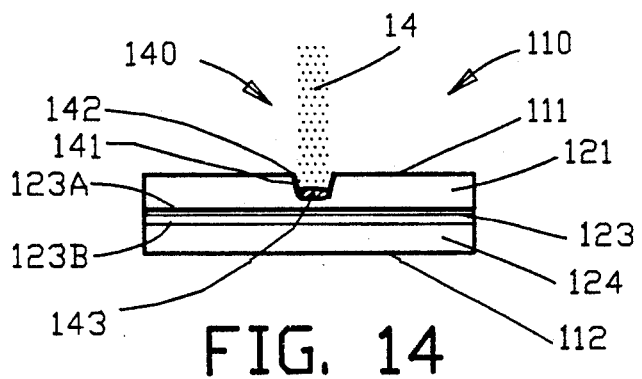
FIG. 14 is a view similar to FIG. 13 illustrating a ceramic crater being formed in an outer polymeric layer by the laser radiation.

FIG. 14 illustrates the penetration of the laser radiation 14 into the outer polymeric layer 121 to form a crater 140. The crater 140 includes a crater sidewall 141 terminating in a crater lip 142 with a moltant bead 143 at the bottom of the crater 140.

Figure 15:
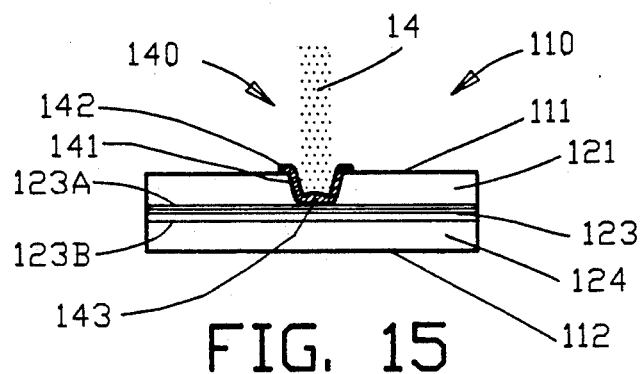
FIG. 15 is a view similar to FIG. 14 illustrating an intermediate mica layer retarding the penetration of the laser radiation therethrough.

FIG. 15 illustrates the further penetration of the laser radiation 14 into the outer polymeric layer 121 with the crater sidewall 142 being enlarged and with the bead 143 being disposed adjacent the intermediate mica layer 123. The intermediate mica layer 123 acts as an insulator to the inner polymeric layer 124.

Figure 16:
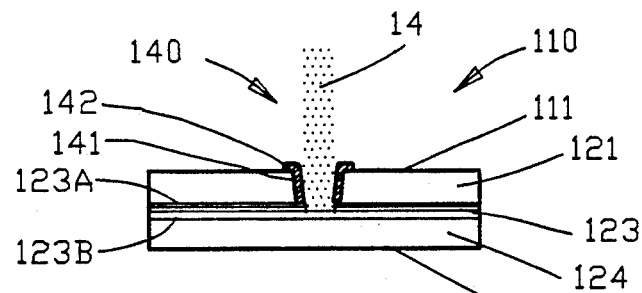
FIG. 16 is a view similar to FIG. 15 illustrating a partial penetration of the intermediate mica layer by the laser radiation.

FIG. 16 illustrates the laser radiation 14 partially burning through the intermediate mica layer 123. The intermediate mica layer 123 continues to thermally insulate the inner polymeric layer 124 from the laser radiation 14. Again, the bead 143 has dissipated and the intermediate mica layer 123 receives the full radiation 14 from the laser 16.

Figure 17:
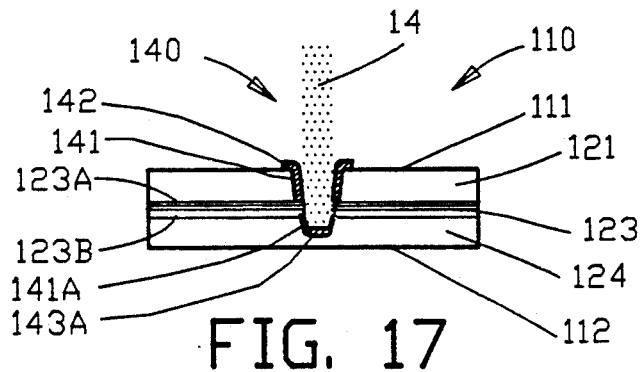
FIG. 17 is a view similar to FIG. 16 illustrating a ceramic crater being formed in an inner polymeric layer by the laser radiation.

FIG. 17 illustrates the completion of penetration of the laser radiation 14 through the mica layer 123 and the commencement of penetration through the inner polymeric layer 124. The crater 140 has reformed with a new bead 143A and a new crater sidewall 141A. Subsequently, the laser radiation 14 burns through the inner polymeric layer 124.

Figure 18:
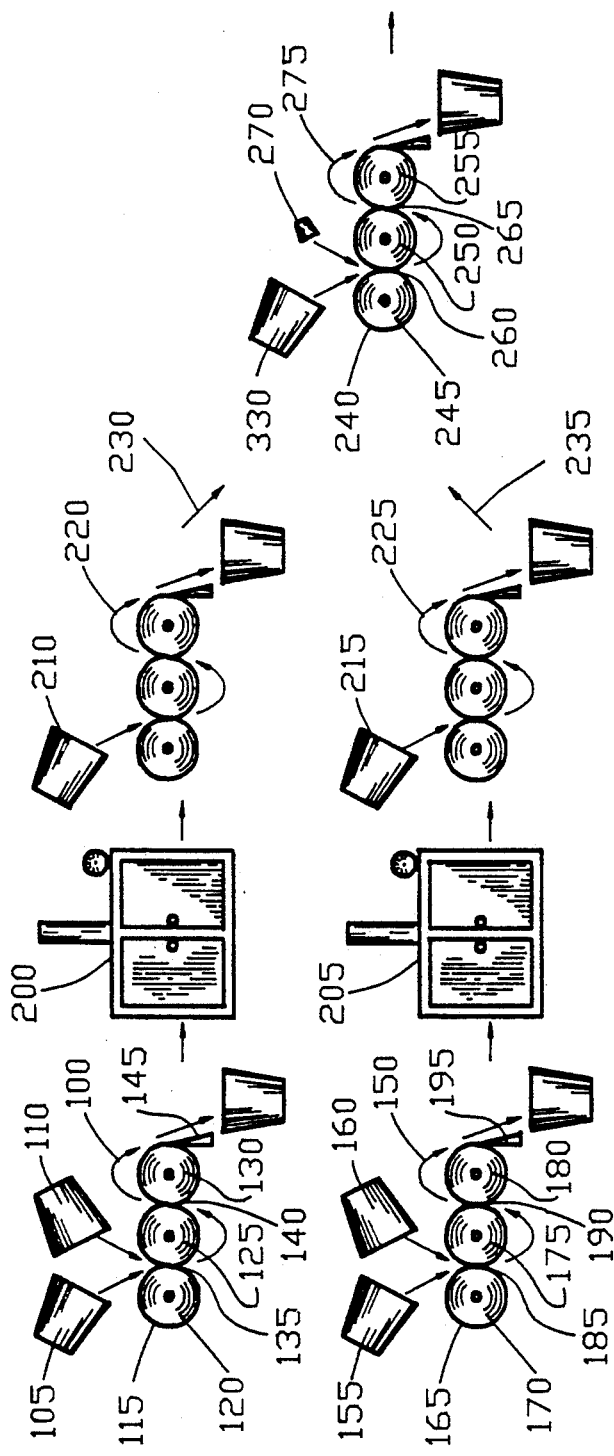
FIG. 18 is a diagram illustrating the steps of forming a polymeric material used in the improved laser radiation barrier of FIGS. 1-10.

FIG. 18 illustrates a process diagram for the preparation of the silicone polymer and filler material of the outer and inner polymeric layer 21 and 24. A first mixture 100 is prepared by mixing 100 parts of a silicone polymer compound 105 and 100 parts of a first filler 110 on a roll mill 115 having three rollers 120, 125 and 130.

The roll mill 115 is similar to the roll mills used for ink or paint. The silicone polymer compound 105 may be a platinum cured room temperature vulcanizing (RTV) silicone compound or a heat curable silicone. Room temperature silicone compounds 105 (RTV) are typically liquids whereas heat curable silicones require a cure temperature and are typically solids with a grease-like consistency. However, virtually any reinforced R gum silicone is expected to function properly in the present invention. The first filler 110 may be a titanium dioxide ($TiO_2$) material.

An optical additive (not shown) may be added to the first mixture 100 to enhance the high temperature stability and/or flame retardancy of the improved laser radiation barrier. The optional additive (not shown) may include a very small amount (approximately 0.5%) of a porcelanized or ceramic clay.

A high friction or shear ratio of approximately 1 to 2 is employed between the rollers 120, 125 and 130. The high friction ratio comprises the ratio of the speed of roller 120 to the speed of roller 125, and the ratio of the speed of roller 125 to the speed of roller 130. The three roll mill with a very high shear permits mixing of the first mixture 100 at a fast rate and enables the first filler 110 to wet more rapidly and with a higher efficiency than other mixing methods.

A gap 135 between the first roller 120 and the second roller 125 is set at substantially 0.060 inches whereas a gap 140 between the second roller 125 and third roller 130 is set at substantially 0.030 inches. A scraper blade 145 is adjusted for minimum clearance with the third roller 130. Typically, two to three passes of the first mixture 100 through the roll mill 115 are generally required to assure substantially complete mixing of the first mixture 100.

After the two to three passes of the first mixture 100 through the roll mill 115, the gap 135 between the first roller 120 and the second roller 125 is readjusted to substantially 0.030 inches and the gap 140 between the second roller 125 and third roller 130 is readjusted to between 0.010 and 0.015 inches. Two to three final passes of the first mixture 100 through the gaps 135 and 140 at the aforementioned re-adjusted gaps 135 and 140 are employed to mix the first mixture 100.

After the mixing of the first mixture 100, the first mixture 100 is placed in an oven 200 at 400 degrees Fahrenheit, for a minimum period of 16 hours to remove the low temperature volatiles. The removal of low temperature volatiles results in low shrinkage in the final product and substantially minimizes the plume smoke from the improved laser radiation barrier 10 when subjected to the laser radiation 14. After the aforementioned processing, the first mixture 100 appears as a white material. An addition of low levels of pigment (not shown) to first mixture 100 may be utilized as a product color code to identify performance levels or the like.

A second mixture 150 is prepared by mixing 100 parts of a silicone polymer compound 155 and 100 parts of a second filler 160. Preferably, the silicone polymer compound 155 is equivalent to silicone polymer compound 105 whereas the second filler 160 may be a Mica material. The silicone polymer compound 155 and the second filler 160 is mixed on a roll mill 165 having three rollers 170, 175 and 180.

A gap 185 between the first roller 170 and the second roller 175 is set at substantially 0.060 inches whereas a gap 190 between the second roller 175 and third roller 180 is set at substantially 0.030 inches. A scraper blade 195 is adjusted for minimum clearance with the third roller 180. Typically, two to three passes of the second mixture 150 through the roll mill 165 are generally required to assure substantially complete mixing of the second mixture 150.

After the two to three passes of the second mixture 150 through the ink or paint mill 165, the gap 185 between the first roller 170 and the second roller 175 is readjusted to substantially 0.030 inches and the gap 190 between the second roller 175 and third roller 180 is readjusted to between 0.010 and 0.015 inches. Two to three final passes of the second mixture 150 through the aforementioned re-adjusted gaps 185 and 190 are employed to mix the second mixture 150.

After the mixing of the second mixture 150, the second mixture 150 is placed in an oven 200 at 400 degrees Fahrenheit, for a minimum period of 16 hours to remove the low temperature volatiles. The removal of low temperature volatiles results in low shrinkage in the final product and substantially minimizes the plume smoke from the improved laser radiation barrier when subjected to laser radiation. After the aforementioned processing, the second mixture 150 appears as a brown or yellowish material.

When the first and second mixtures 100 and 150 are devolatilized the first and second devolatilized mixtures 210 and 215 are freshened by individual mixing the first and second mixtures 100 and 150 on three roll mills 220 and 225, respectively. After the first and second devolatilized mixtures 210 and 215 are freshened, equal amounts of the devolatilized first and second mixtures 230 and 235 are weighed and blended together on a roll mill 240 having three rollers 245, 250 and 255. The gap 260 between the first roller 245 and the second roller 250 of the roll mill 240 is set at 0.125 inches whereas the gap 265 between the second roller 250 and the third roller 255 is set at 0.062 inches.

A preliminary blending of the first devolatilized mixture 230 (white material) and the second devolatilized mixture 235 (brown or yellowish material) is determined when the cross blend of the first and second mixtures 230, 235 on the roll mill 240 has a marbleized color. A final blending to provide a homogenous mixture of the first and second mixtures 230 and 235 is indicated by a uniform color. Following the completion of final blending, the mixture is ready for catalysis and subsequent quality control measurements.

Preferably, 10 parts of a catalyst 270 is added to the blend of the first and second mixtures 230 and 235 on the roll mill 240. The rollers 245, 250 and 255 must remain cool since catalyst 270 to prevent curing or partial curing of the RTV silicone components 105 and 155 of first and second mixtures 230 and 235 respectively on the roll mill 240. Typically, the final catalyzed mixture 275 will cure at room temperature in a few hours. Alternately, final catalyzed mixture 275 may be accelerated to cure in a few minutes at 300 degrees fahrenheit.

Figure 19:
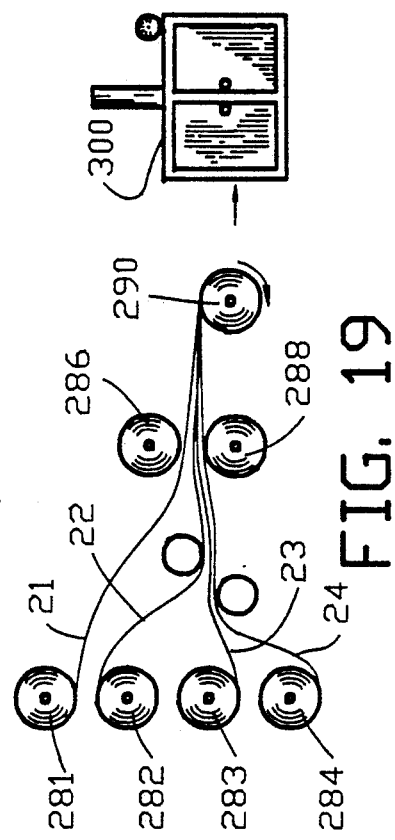
FIG. 19 is a diagram illustrating the steps of forming the first embodiment of the improved laser radiation barrier of FIGS. 1-10.

FIG. 19 represents a process of forming the improved laser radiation barrier 10 of FIGS. 1–10 comprising a roll 281 of the outer polymeric layer 21, a roll 282 of the metallic barrier layer 22, a roll 283 of the intermediate mica layer 23 and a roll 284 of the inner polymeric layer 24. A sheet of outer polymeric layer 21 from roll 281, a sheet of the metallic barrier layer 22 from roll 282, a sheet of the intermediate mica layer 23 from roll 283 and a sheet of the inner polymeric layer 24 from roll 283 are directed through press rollers 286 and 288. The press rollers 286 and 288 press the outer polymeric layer 21, the metallic barrier layer 22, the intermediate mica layer 23 and the inner polymeric layer 24 into the improved laser radiation barrier 10. The improved laser radiation barrier 10 is then placed in an oven 290 for final curing.

Figure 20:
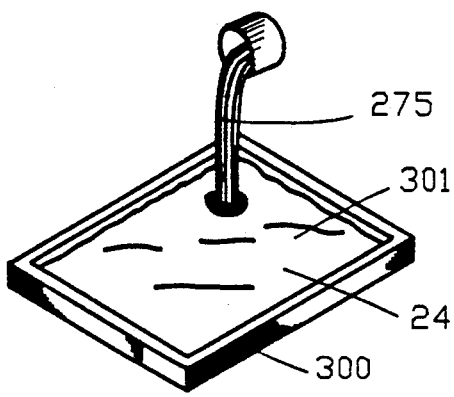
FIG. 20-25 illustrate the steps of forming the improved laser radiation barrier of FIGS. 1-10 in a molding process.

FIGS. 20-25 illustrate an alternative process for the preparation of the laser radiation barrier 10 with a mold 300. FIG. 20 illustrates a first layer 301 of final catalyzed mixture 275 being placed in the mold 300 to form the inner polymeric layer 24.

Figure 21:
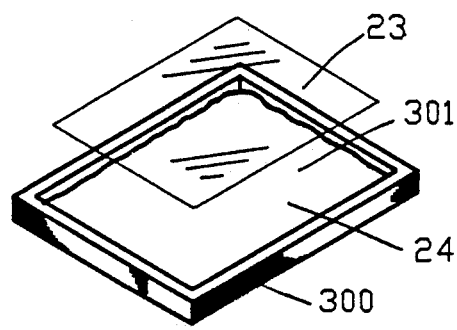

FIG. 21 shows the intermediate mica sheet 23 being positioned proximate first layer 301 of final catalyzed mixture 275 in the mold 300. Preferably, the intermediate mica sheet 23 comprises a magnesia based or a pot ash based mica. Both rigid natural mica as well as mica paper may be utilized in the present invention. The purpose of the mica sheet 23 is to provide thermal insulation for the inner polymer layer 24. If maximum flexibility is required, a high flex mica material may be utilized which may be produced by impregnating a mica sheet with a very high heat resistant silicone resin with the thickness of the silicone resin between 0.003 inches to 0.010 inches.

Natural mica occurs as either muscovite mica, commonly referred to as potash mica or philogopite mica, commonly referred to as magnesia mica. The magnesia mica is preferred for use in the present invention due to superior high temperature properties of magnesia mica. The magnesia mica is moderately flexible but cannot be use where high flexibility is required such as small catheter tubes or the like. In high flexibility applications, micapaper is the desired form of mica. In mica paper, small mica pieces are bonded to a flexible substrate such as paper by suitable adhesive binder. The small mica pieces enable a flexing between the mica joints to provide a suitable material for high flexibility requirements. One product of micropaper is sold under the trademark COGEMICA by Cogebi, Inc. of Dover, N.H. Preferably, magnesia mica is used for all applications unless high flexibility is required due to the superior thermal properties of the magnesia mica over the micapaper.

Figure 22:
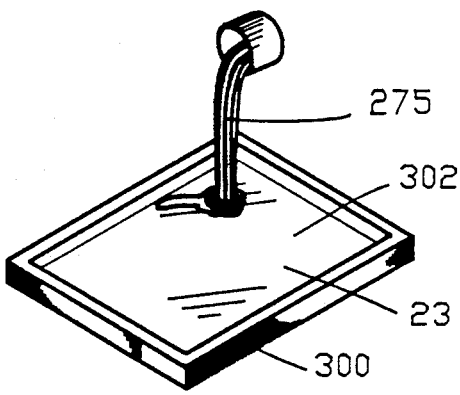

FIG. 22 illustrates second layer 302 of final catalyzed mixture 275 being placed in the mold 300 proximate the intermediate mica sheet 23.

Figure 23:
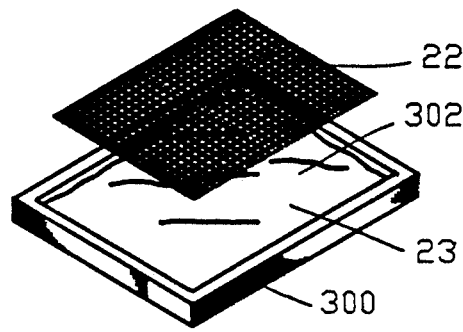
Figure 24:
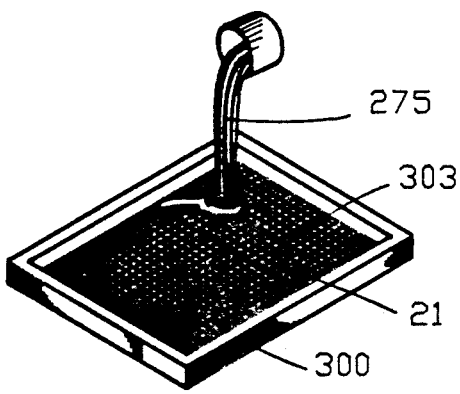
Figure 25:
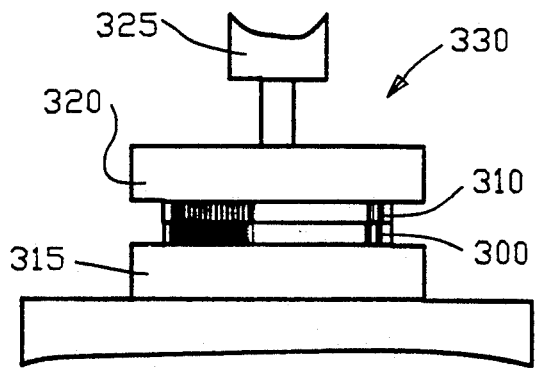

FIG. 23 illustrates the perforated metallic barrier 22 being positioned proximate second layer 302 of final catalyzed mixture 275 in the mold 300. Preferably, the metallic barrier 22 is a flat copper metal foil to provide a uniform heat distribution in the improved laser radiation barrier 10. Although flat copper metal foil has been disclosed as a material for the perforated metallic barrier 22, other material such as steel, silver, nickel, gold or other metallic material may be used with the present invention. The favorable thermal conductivity of copper, the cost effectiveness, and the quality of the copper available indicates that copper is the material of choice for the present invention.

Copper has a high melting point around 1970 degrees fahrenheit and has one of the best thermal conductivity "K" factors of common metals through a wide range of temperatures. Copper has "K" factor of 224 at 30 degrees fahrenheit and when temperatures reach nearly 1100 degrees fahrenheit the "K" factor may reduce to 204, indicating a very stable material relative to thermal conductivity. By contrast, aluminium has "K" factor of 117 at 32 degrees fahrenheit and a "K" factor of substantially 0 as temperatures near 500 degrees fahrenheit.

The perforated metallic barrier 22 is produced by a special die cutting process wherein the perforations 26 are formed in a continuous metallic sheet. The perforated metallic barrier 22 is in contrast to a metallic screen wherein the screen wire may be uneven, twisted and not completely bounded at the intersections or interstices thereof. Accordingly, the intersections or interstices of a wire screen may produce thermal imbalances and hot spots thus reducing the thermal conductivity of metallic screen relative to a perforated metallic foil.

The perforated metallic barrier 22 has no raised sections resulting in a substantially flat foil having mesh from between 130 to 1400 or approximately 130 to 1400 openings per square inch. If a flexible improved laser radiation barrier 10 is desired, the perforated metallic barrier 22 may be annealed to reduce the resiliency of the improved laser radiation barrier 10. One product of mesh is sold under the trademark MICROGRID by the Delker Corporation of Bradford, Conn.

FIG. 23 illustrates a third layer 303 of final catalyzed mixture 275 being placed in the mold 300 on perforated metallic barrier 22 to form the outer polymeric layer 21. The outer polymeric layer 21 substantially mechanically encapsulates the perforated metallic barrier 300 since final catalyzed mixture 275 flows through the perforations 26 of perforated metallic barrier 22.

The mold 300 is placed on the lower heated press platen 315 of the heated press 330 and a mold cover 310 is positioned on the mold 300. The application of force from pressure means 325 on upper the heated press platen 320 of the heated press 330 provides the heat and pressure required to cure the final the laser radiation barrier 10.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A process for producing an improved laser radiation barrier for shielding a surface from laser radiation comprising the steps of:

mixing a first mixture comprising a silicone polymer compound and a first filler on a roll mill;

heating the first mixture to liberate volatile components;

mixing a second mixture comprising a silicone polymer compound and a second filler on a roll mill;

heating the second mixture to liberate volatile components;

mixing the first and the second mixtures with a catalyst on a roll mill to create a final catalyzed mixture;

placing a first layer of the final catalyzed mixture in a mold;

placing a mica sheet in the mold upon the first layer of the final catalyzed mixture;

placing a second layer of the final catalyzed mixture in the mold upon the mica sheet; and curing the final catalyzed material.

2. A process for producing an improved laser radiation barrier for shielding a surface from laser radiation as set forth in claim 11, wherein the silicon polymer compound comprises room temperature vulcanizing (RTV) silicone polymers and platinum based catalyst materials.

3. A process for producing an improved laser radiation barrier for shielding a surface from laser radiation as set forth in claim 1, wherein the silicone polymer compound comprises silica reinforced R gum silicone polymers and peroxide based catalyst materials.

4. A process for producing an improved laser radiation barrier for shielding a surface from laser radiation as set forth in claim 1, wherein the first filler comprises Titanium Dioxide (TiO$_2$).

5. A process for producing an improved laser radiation barrier for shielding a surface from laser radiation as set forth in claim 1, wherein the second filler comprises MICA.

6. A process for producing an improved laser radiation barrier for shielding a surface from laser radiation as set forth in claim 1, wherein the roll mill comprises a three roll mill operated at a high friction ratio.

7. A process for producing an improved laser radiation barrier for shielding a surface from laser radiation as set forth in claim 1, wherein the final catalyzed material comprises a ceramic clay.

8. A process for producing an improved laser radiation barrier for shielding a surface from laser radiation comprising the steps of:

preparing a first mixture of 100 parts silicone polymer compound and 100 parts first filler;

mixing the first mixture on a roll mill;

baking the first mixture in an oven at a temperature of 400 degrees fahrenheit for a minimum of 16 hours;

preparing a second mixture of 100 parts silicone polymer compound and 100 parts second filler;

mixing the second mixture on a roll mill;

baking the second mixture in an oven at a temperature of 400 degrees fahrenheit for a minimum of 16 hours;

mixing the first and second mixtures with a catalyst on a roll mill to prepare a final catalyzed mixture;

placing a first layer of the final catalyzed mixture in a mold;

placing a mica sheet in the mold upon the first layer of the final catalyzed mixture;

placing an intermediate layer of the final catalyzed mixture in the mold upon the mica sheet;

placing a metallic barrier having a plurality of perforations upon the intermediate layer of the final catalyzed mixture;

placing a second layer of the final catalyzed mixture in the mold upon the metallic barrier; and curing the final catalyzed material;

9. A process for producing an improved laser radiation barrier for shielding a surface from laser radiation as set forth in claim 8, wherein the silicone polymer compound comprises room temperature vulcanizing (RTV) silicone polymers and platinum based catalyst materials.

10. A process for producing an improved laser radiation barrier for shielding a surface from laser radiation as set forth in claim 8, wherein the silicone polymer compound comprises silica reinforced R gum silicone polymers and peroxide based catalyst materials.

11. A process for producing an improved laser radiation barrier for shielding a surface from laser radiation as set forth in claim 8, wherein the first filler comprises Titanium Dioxide (TiO$_2$).

12. A process for producing an improved laser radiation barrier for shielding a surface from laser radiation as set forth in claim 8, wherein the second filler comprises MICA.

13. A process for producing an improved laser radiation barrier for shielding a surface from laser radiation as set forth in claim 8, wherein the roll mill comprises a three roll paint or ink mill operated at a high friction ratio.

14. A process for producing an improved laser radiation barrier for shielding a surface from laser radiation as set forth in claim 8, wherein the final catalyzed material comprises a ceramic clay.

15. A process for producing an improved laser radiation barrier for shielding a surface form laser radiation as set forth in claim 8, wherein the silicone polymer compound comprises room temperature vulcanizing (RTV) silicone polymers and platinum based catalyst materials.

* * * * *